(12) United States Patent
Brandt et al.

(10) Patent No.: US 7,846,896 B2
(45) Date of Patent: Dec. 7, 2010

(54) PEG CONJUGATES OF NK4

(75) Inventors: Michael Brandt, Iffeldorf (DE);
Apollon Papdimitriou, Bichl (DE)

(73) Assignee: Hoffman-La Roche Inc., Nutley, NJ (US)

( * ) Notice: Subject to any disclaimer, the term of this patent is extended or adjusted under 35 U.S.C. 154(b) by 126 days.

(21) Appl. No.: 11/869,797

(22) Filed: Oct. 10, 2007

(65) Prior Publication Data

US 2008/0085857 A1     Apr. 10, 2008

Related U.S. Application Data

(62) Division of application No. 10/081,309, filed on Feb. 21, 2002, now abandoned.

(30) Foreign Application Priority Data

Feb. 23, 2001   (EP) ................... 01104640

(51) Int. Cl.
*A61K 38/18*   (2006.01)
*C07K 38/00*   (2006.01)

(52) U.S. Cl. .......................... 514/8; 530/350
(58) Field of Classification Search ........................ None
See application file for complete search history.

(56) References Cited

U.S. PATENT DOCUMENTS

| 5,766,581 | A | * | 6/1998 | Bartley et al. .............. 424/85.1 |
| 5,977,310 | A | | 11/1999 | Namiki et al. |
| 6,025,324 | A | | 2/2000 | Bailon et al. |
| 6,340,742 | B1 | | 1/2002 | Burg et al. |
| 6,528,485 | B1 | | 3/2003 | Veronese et al. |
| 6,583,272 | B1 | | 6/2003 | Bailon |
| 2002/0115833 | A1 | | 8/2002 | Burg et al. |

FOREIGN PATENT DOCUMENTS

| EP | 0 741 187 | 11/1996 |
| EP | 0 816 381 | 1/1998 |
| EP | 08 16381 | 7/1998 |
| EP | 1 064 951 | 1/2001 |
| WO | WO 93/23541 | 11/1993 |
| WO | WO 94/13322 | 6/1994 |
| WO | 9611953 | 4/1996 |
| WO | WO 98/31383 | 7/1998 |
| WO | 99/43813 | 9/1999 |
| WO | WO 99 55377 | 11/1999 |
| WO | WO 00 21574 | 4/2000 |

OTHER PUBLICATIONS

Date, K., et al., FEBS Letters vol. 420 (1997) pp. 1-6.
Date, K., et al., Oncogene (1998) vol. 17 pp. 3045-3054.
Kuba, K., et al. Cancer Research (2000) vol. 60, pp. 6737-6743.
Uematsu Y., et al., Journal of Pharmaceutical Sciences (Jan. 1999), vol. 88 No. 1, pp. 131-135.
Gaertner, H., et al., Bioconjugate Chem. (1996) vol. 7 pp. 38-44.
Francis, G.E., et al., International Journal of Hematology, vol. 68 (1998) pp. 1-18.
Tsutsumi, Y. et al. Thrombosis & Haemostasis vol. 77, No. 1 (1997) pp. 168-173.
Tsutsumi, Y. et al., Proceedings of the National Academy of Sciences of the United States, vol. 97, No. 15 (Jul. 18, 2000) pp. 8548-8553).
Heinzerling, L., et al., Dermatology (2000) vol. 201, pp. 154-157.
Tsutsumi, Y., Journal of Pharmacology & Experimental Therapeutics vol. 278 No. 3 (1996) pp. 1006-1011.
Reddy, R., et al. Annals of Pharmacotherapy vol. 34, No. 7-8 (Jul. 2000) pp. 915-923.
Bailon, P., Bioconjugate Chem. vol. 12 (Feb. 16, 2001) pp. 195-202.
Parr, C., et al., Int. J. Cancer vol. 85 (2000) pp. 563-570.

* cited by examiner

*Primary Examiner*—Robert Landsman
*Assistant Examiner*—Gyan Chandra
(74) *Attorney, Agent, or Firm*—George W. Johnston; Dennis P. Tramaloni

(57) ABSTRACT

The present invention provides a conjugate consisting essentially of a NK4 molecule and a polyethylene glycol group having a molecular weight of from about 20 to about 40 kDa. The invention also provides a composition in which the monoPEGylated conjugates comprise at least 90% of the total of pegylated NK4 molecules and unpegylated NK4 molecules in the composition. Also provided is a composition in which the monoPEGylated conjugates comprise conjugates in which the PEG groups are attached to groups randomly selected from the lysine side chains of NK4 molecules and the N-terminal amino groups of NK4 molecules. A method for the treatment of cancer by administering 1 to 30 mg monoPEGylated NK4 per kg per day is further provided.

7 Claims, 4 Drawing Sheets

PEG CONJUGATES OF NK4

PRIORITY TO RELATED APPLICATION(S)

This application is a division of U.S. application Ser. No. 10/081,309, filed Feb. 21, 2002, now Pending; which claims the benefit of European Application No. 01104640.6, filed Feb. 23, 2001. The entire contents of the above-identified applications are hereby incorporated by reference.

BACKGROUND OF THE INVENTION

Hepatocyte growth factor (HGF/SF) is a polypeptide identified and purified by Nakamura, T., et al., Biochem. Biophys. Res. Commun. 22 (1984) 1450-1459. It was further found that hepatocyte growth factor is identical to scatter factor (SF), Weidner, K. M., et al., Proc. Natl. Acad. Sci. USA 88 (1991) 7001-7005. HGF is a glycoprotein with a molecular weight of about 100 kDa involved in the development of a number of cellular phenotypes including proliferation, mitogenesis, formation of branching tubules and, in the case of tumor cells, invasion and metastasis. For a status review, see Stuart, K. A., et al., International Journal of Experimental Pathology 81 (2000) 17-30. Both rat HGF and human HGF have been sequenced and cloned (Miyazawa, K. et al., Biochem. Biophys. Res. Comm. 163 (1989) 967-973; Nakamura, T., et al., Nature 342 (1989) 440-443; Seki, T., et al., Biochem. and Biophys. Res. Comm. 172 (1990) 321-327; Tashiro, K., et al., Proc. Natl. Acad. Sci. USA 87 (1990) 3200-3204; Okajima, A., et al., Eur. J. Biochem. 193 (1990) 375-381). The pharmacokinetics and pharmacological effects of an HGF lacking the first five N-terminal amino acids (dHGF) were investigated by Uematsu, Y., et al., J. Pharm. Sciences 88 (1999) 131-135. It was found that the serum concentration of dHGF decreased rapidly and therefore infusion would be preferred against bolus injection as administration route.

U.S. Pat. No. 5,977,310 describes PEG-modified HGF. Such PEG-modified HGF has a prolonged clearance in vivo and has the same physiological activity as HGF. However, according to U.S. Pat. No. 5,977,310, it is only possible to prolong the half life of HGF from 59.2 minutes to 76.7 minutes or 95.6 minutes, respectively (see Example 5 of U.S. Pat. No. 5,977,310). It is further suggested in this patent that the molar amount of the PEG reagent may be selected from the range of from 5 to 100 times of the molar weight of HGF. In the case of modifying an amino group of lysine or the N-terminus of protein, a preferred molar range of the PEG reagent is of from 10 to 25 times of the molar weight of HGF. The molecular weight of the attached PEG chain was about 10 kDa. Methods for the synthesis of conjugates consisting of PEG and polypeptides such as HGF are also described in WO 94/13322. These conjugates are linked together at predefined positions as random conjugation leads, according to the authors, to the introduction of polymeric moieties into domains of the molecule that mediate the therapeutically or diagnostically desirable activities. Consequently, the molecules may acquire a prolonged half-life in vivo and, in the case of heterologous proteins, reduced immunogenicity, but at the expense of a significant or complete loss of the desired biological activities (see, e.g., Kitamura, K., et al., Cancer Res. 51 (1991) 4310-4315 and Maiti, P. K., et al., Int. J. Cancer Suppl. 3 (1988) 17-22). PEGylated IFN-α shows, for example, only 7% of the potency compared to non-PEGylated IFN-α (Bailon, P., Bioconjugate Chem. 12 (2001) 195-202).

It was further found that an HGF/SF fragment, termed NK4, consisting of the N-terminal hairpin domain and the four kringle domains of HGF/SF, has pharmacological properties that are completely different from those of HGF/SF, and is an antagonist to the influence of HGF/SF on the motility and the invasion of colon cancer cells, and is, in addition, an angiogenesis inhibitor that suppresses tumor growth and metastasis (WO 93/23541; Parr, C., et al., Int. J. Cancer 85 (2000) 563-570; Kuba, K., et al., Cancer Res. 60 (2000) 6737-6743; Date, K., et al., FEBS Letters 420 (1997) 1-6; Date, K., et al., Oncogene 17 (1989) 3045-3054; Tomioka, D., et al., Cancer Res. 61 (2001) 7518-7524).

As emerges from Kuba, K., et al., Cancer Res. 60 (2000) 6737-6743, in animal experiments, for detecting an effect of NK4 on lung metastases, NK4 had to be infused continuously over a period of two weeks.

It is known that the attachment of polymers to certain polypeptides may increase the serum half life of such polypeptides. This was found, for example, for PEGylated Interleukin-6 (EP 0 442 724) or Interleukin-2 (WO 90/07938) and erythropoietin (WO 01/02017). However, the attachment of polyethylene glycol and other polymers does not necessarily lead to prolongation of their serum half lives. It is known, for example, that the conjugation of different polyethylene glycols to Interleukin-8, G-CSF and other interleukins results in the production of molecules with impaired properties (Mehvar, R., J. Pharm. Pharm. Sci. 3 (1) (2000) 125-136). Thus, the outcome of a PEGylation of a polypeptide is highly unpredictable. Gaertner, H. F., and Offord, R. E., Bioconjugate Chem. 7 (1996) 38-44 describes the site-specific attachment of PEG to the amino terminus of proteins. Gaertner et al. state (as already mentioned in WO 94/13222, see above) that PEGylation presents a big problem if the attachment sites cannot be precisely controlled, as this might have important implications for protein stability and function.

Francis, G. E., et al., Int. J. Hematol. 68 (1998) 1-18 present an overview of PEGylation of cytokines and other therapeutic proteins. Francis et al. state that with the majority of methods of PEGylation, substantial reduction of bioactivity has been reported (typically, 20-95%). According to Francis et al., PEGylation of proteins is always based on trial and error and virtually all parameters of such a PEGylation can have a surprising and very profound effect on the functionality of the product. Tsutsumi, Y., et al., Thromb. Haemost. 77 (1997) 168-173 describes the PEGylation of Interleukin-6. According to Tsutsumi et al., about 54% of the lysine amino groups of IL-6 were coupled with PEG with a molecular weight of 5 kDa per PEG group. Tsutsumi et al., in Proc. Natl. Acad. Sci. USA 97 (2000) 8548-8553, describe the chemical modification of an immunotoxin by PEG. As random PEGylation was accompanied by a significant loss of specific cytotoxic activity, Tsutsumi performs a site-specific PEGylation by using an immunotoxin mutant with one or two additional cysteines which are used for PEG coupling. Heinzerling, L., et al., Dermatol. 201 (2000) 154-157 describes the coupling of PEG to Interferon-α with a molecular weight of 5 kDa. Tsutsumi, Y., et al., in J. Pharmacol. Exp. Ther. 278 (1996) 1006-1011, describe the PEG modification of TNF-α, whereby the molecular weight of the PEG groups used is again 5 kDa. As the PEGylated TNF-α applied has a molecular weight of at least 84 kDa (by a molecular weight of 17 kDa of TNF-α) there are at least 13 5-kDa PEG groups attached to TNF-α.

PEGylation of proteins and its pharmacological effects are also reviewed by Reddy, K. R., Ann. Pharmacotherapy 34 (2000) 915-923. Again it is stated that PEGylation of therapeutic proteins must be carefully evaluated. Each protein is, according to Reddy et al., different, requires different optimization chemistry and therefore the influence of PEGylation cannot be predicted.

SUMMARY OF THE INVENTION

The present invention provides a conjugate consisting of a NK4 molecule and a polyethylene glycol group having a molecular weight of from about 20 to about 40 kDa.

The present invention provides a composition comprising conjugates of NK4 monoPEGylated with polyethylene glycol groups that have a molecular weight of from about 20 to about 40 kDa, wherein the conjugates comprise conjugates in which the polyethylene glycol groups are randomly attached to groups of the NK4 molecules selected from the lysine side chains of NK4 molecules and the N-terminal amino groups of NK4 molecules.

The present invention also provides a composition comprising conjugates of NK4 monoPEGylated with polyethylene glycol groups that have a molecular weight of from about 20 to about 40 kDa, wherein the monoPEGylated conjugates comprise at least 90% of the total of pegylated NK4 molecules and unpegylated NK4 molecules in the composition.

The present invention further provides a method for the treatment of cancer wherein 1 to 30 mg of the monoPEGylated NK4 is administered per kg per day to a patient in need of treatment.

BRIEF DESCRIPTION OF THE SEQUENCES

SEQ ID NO:1 shows the DNA and polypeptide sequence of NK4.

SEQ ID NO:2 shows the polypeptide sequence of NK4.

DETAILED DESCRIPTION OF THE INVENTION

Figure 1:
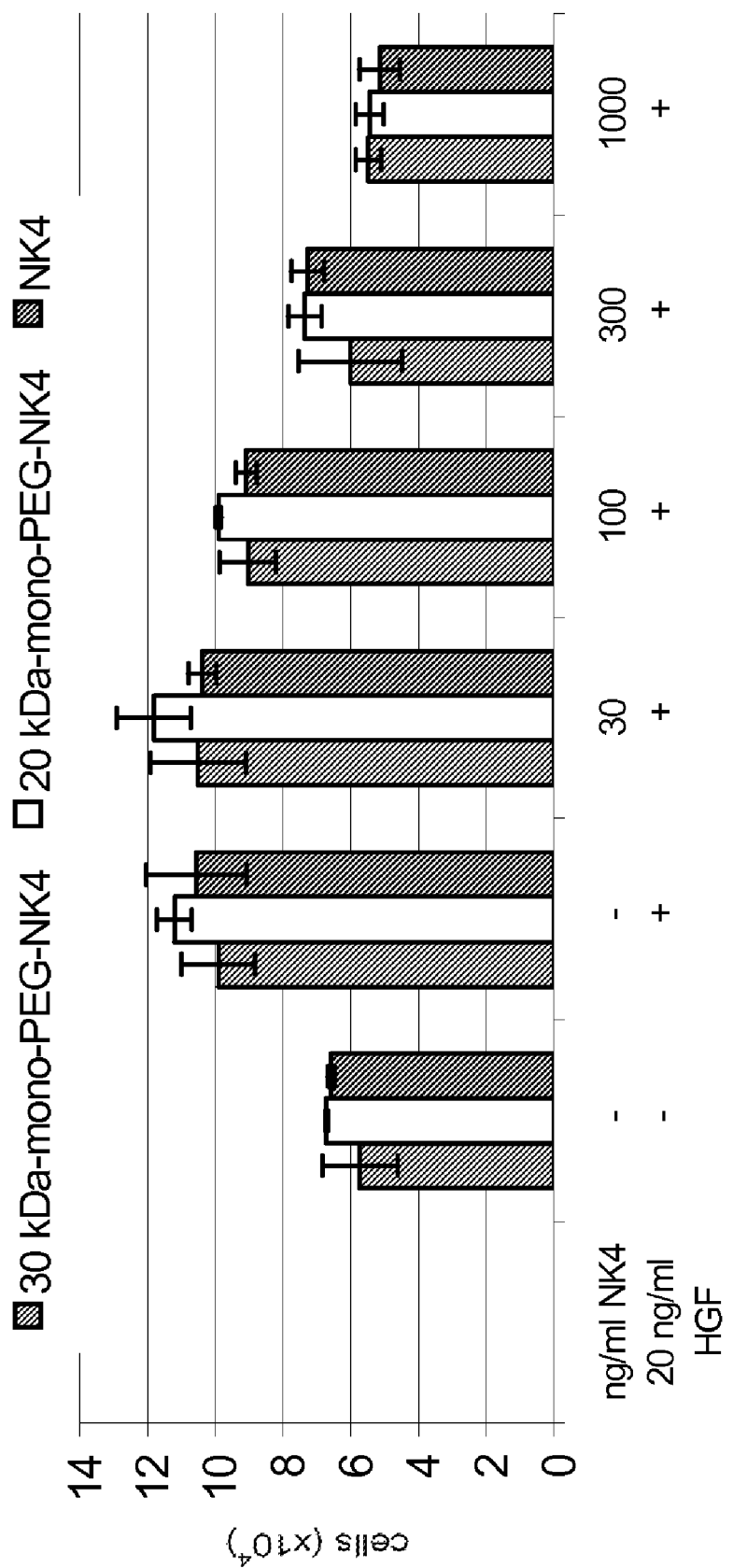
FIG. 1 Inhibition of HGF-induced HUVEC proliferation by NK4, 20 kDa-mono-PEG-NK4 and 30 kDa-mono-PEG-NK4.

The present invention provides NK4 conjugates consisting of NK4 being covalently linked to one polyethylene glycol (PEG) group of from about 20 to about 40 kDa (monoPEGylated NK4), preferably via an ε-amino group of NK4 lysine or the N-terminal amino group. Most preferably, NK4 is randomly PEGylated at one amino group out of the group consisting of the ε-amino groups of NK4 lysine and the N-terminal amino group. Surprisingly, it has been found that monoPEGylated NK4 according to the invention has superior properties in regard to the therapeutic applicability of NK4 or otherwise PEGylated NK4.

Human HGF is a disulfide-linked heterodimer, which can be cleaved in an α-subunit of 463 amino acids and a β-subunit of 234 amino acids, by cleavage between amino acids R494 and V495. The N-terminus of the α-chain is preceded by 31 amino acids started with a methionine group. This segment includes a signal sequence of 31 amino acids. The α-chain starts at amino acid 32 and contains four kringle domains. The so-called "hairpin domain" consists of amino acids 70-96. The kringle 1 domain consists of amino acids 128-206. The kringle 2 domain consists of amino acids 211-288, the kringle 3 domain consists of amino acids 305-383, and the kringle 4 domain consists of amino acids 391-469 of the α-chain, approximately. There exist variations of these sequences, essentially not affecting the biological properties of NK4 (especially not affecting its activities antagonistic to HGF and its antiangiogenic activities), which variations are described, for example, in WO 93/23541. Also the length of NK4 can vary within a few amino acids as long as its biological properties are not affected.

NK4 is composed of the N-terminal 447 amino acids of the HGF/SFα-chain, which includes the above-mentioned hairpin domain and the four kringle domains. It can be produced recombinantly, either by the production of recombinant human HGF/SF and digestion with elastase (Date, K., FEBS Letters 420 (1997) 1-6) or by recombinant expression of an NK4 encoding nucleic acid in appropriate host cells, as described below. NK4 glycoprotein has a molecular weight of about 57 kDa (52 kDa for the polypeptide part alone) and has the in vivo biological activity of causing inhibition of tumor growth, angiogenesis and/or metastasis.

"MonoPEGylated NK4" as used herein means that NK4 has attached covalently one polyethylene glycol group with a molecular weight of from about 20 to about 40 kDa. The group can be attached, preferably randomly, at one of various sites of the NK4 molecule, preferably, however, at one of the most reactive sites, e.g., of the lysine side chains and the N-terminal amino group. MonoPEGylated NK4 (which therefore preferably is a mixture of monoPEGylated NK4 molecules, PEGylated at different sites which are the ε-amino groups of NK4 lysine and the N-terminal amino group) is at least 90% of the preparation, and most preferably, the monoPEGylated NK4 is 92%, or more, of the preparation of the present invention. The monoPEGylated NK4 preparations according to the invention are homogeneous enough to display the advantages of a substantially homogeneous preparation, e.g., in a pharmaceutical application. "Substantially homogeneous" as used herein means that the only PEG-NK4 conjugate molecules produced, contained or used are those having one PEG group attached. The monoPEGylated NK4 preparation of the present invention may contain unreacted (i.e., lacking PEG group) protein and/or multiPEGylated NK4. As ascertained by peptide mapping and N-terminal sequencing, one example below provides a preparation which is at least 90% monoPEG-NK4 conjugate and at most 2% unreacted protein.

The PEG polymer molecules used according to the invention have a molecular weight of from about 20 to about 40 kDa, whereby PEG polymers with about 20, 30 or 40 kDa are preferred (by "molecular weight" as used here there is to be understood the mean molecular weight of the PEG; the term "about" indicates that in said PEG preparations, some molecules will weigh more and some less than the stated molecular weight).

"PEG or PEG group" according to the invention means a residue containing poly(ethylene glycol) as an essential part. Such a PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. Especially preferred are PEGs with two PEG side-chains (PEG2) linked via the primary amino groups of a lysine (Monfardini, C., et al., Bioconjugate Chem. 6 (1995) 62-69). As PEG polymers with a molecular weight of 20-30 kDa linear PEG molecules are preferred and as PEG polymers with a molecular weight of more than 30 kDa, especially with 40 kDa, branched PEGs are preferred. As PEG 40 kDa a two-armed PEG (PEG2) is particularly preferred.

According to the invention a method is provided for the production of a monoPEGylated NK4 preparation. PEGylation of NK4 can be performed according to the methods of the state of the art, for example by reaction of NK4 with electrophilically active PEGs (supplier: Shearwater Corp., USA). Preferred PEG reagents are, e.g., N-hydroxysuccinimidyl propionates (PEG-SPA) or butanoates (PEG-SBA) or branched N-hydroxysuccinimides such as mPEG2—NHS (Monfardini, C., et al., Bioconjugate Chem. 6 (1995) 62-69). Such methods result in an NK4 polypeptide which is randomly PEGylated at an ε-amino group of an NK4 lysine or the N-terminal amino group. Not randomly, N-terminally PEGylated NK4 can be produced according to WO 94/01451.

In a preferred embodiment of the invention, said NK4 is covalently linked to one poly(ethylene glycol) group of the formula

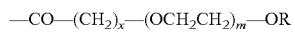
—CO—(CH$_2$)$_x$—(OCH$_2$CH$_2$)$_m$—OR with the —CO (i.e. carbonyl) of the poly(ethylene glycol) group forming an amide bond with one of the amino groups of NK4; R being lower alkyl; x being 2 or 3; m being from about 450 to about 950; and n and m being chosen so that the molecular weight of the conjugate minus the NK4 protein is from about 20 to 40 kDa. As amino group of NK4 the ε-amino group of NK4 lysine is the available (free) amino group.

More specifically, the above conjugates may be represented by formula (I)

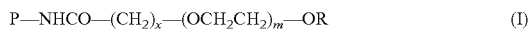
P—NHCO—(CH$_2$)$_x$—(OCH$_2$CH$_2$)$_m$—OR  (I)

wherein P is the group of an NK4 protein as described herein, (i.e. without the amino group or amino groups which form an amide linkage with the carbonyl shown in formula (I); and wherein R is lower alkyl; x is 2 or 3; m is from about 450 to about 950 and is chosen so that the molecular weight of the conjugate minus the NK4 protein is from about 20 to about 40 kDa. As used herein, the given ranges of "m" have an orientational meaning. The ranges of "m" are determined in any case, and exactly, by the molecular weight of the PEG group.

In a further preferred embodiment of the invention, said NK4 is covalently linked to one poly(ethylene glycol) group of the formula

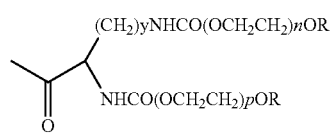

wherein y is 1 to 4, preferably 4, n and p together are chosen such that the molecular weight of the conjugate minus the NK4 protein is from about 20 to 40 kDa, preferably 40 kDa, and n and p differ by not more than 25%, preferably by not more than 10%, and most preferably are identical, and R is lower alkyl.

As used herein, "lower alkyl" means a linear or branched alkyl group having from one to six carbon atoms (C$_1$-C$_6$ alkyl). Examples of lower alkyl groups include methyl, ethyl and isopropyl. In accordance with this invention, R is any lower alkyl. Conjugates in which R is methyl are preferred.

The symbol "m" represents the number of ethylene oxide groups (OCH$_2$CH$_2$) in the poly(ethylene oxide) group. A single PEG subunit of ethylene oxide has a molecular weight of about 44 daltons. Thus, the molecular weight of the conjugate (excluding the molecular weight of the NK4) depends on the number "m". In the conjugates of this invention "m" is from about 450 to about 950 (corresponding to a molecular weight of about 20 kDa to about 40 kDa). The number m is selected such that the resulting conjugate of this invention has a physiological activity comparable to unmodified NK4, which activity may represent the same as, more than, or a fraction of the corresponding activity of unmodified NK4. A molecular weight of "about" a certain number means that it is within a reasonable range of that number as determined by conventional analytical techniques. The number "m" is selected so that the molecular weight of each poly(ethylene glycol) group that is covalently linked to the NK4 protein is from about 20 kDa to about 40 kDa.

The compound of formula (I) can be prepared, for example, from a known activated polymeric material:

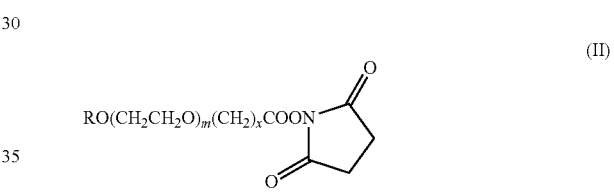

in which R and m are as described above, by condensing the compound of Formula II with the NK4 protein. Compounds of formula (II) in which x is 3 are alpha-lower alkoxybutyric acid succinimidyl esters of poly(ethylene glycol) (lower alkoxy-PEG-SBA). Compounds of formula (II) in which x is 2 are alpha-lower alkoxypropionic acid succinimidyl esters of poly(ethylene glycol) (lower alkoxy-PEG-SPA). Any conventional method of reacting an activated ester with an amine to form an amide can be utilized. In the reaction described above, the exemplified succinimidyl ester is a leaving group causing the amide formation. The use of succinimidyl esters such as the compounds of formula II to produce conjugates with proteins are disclosed in U.S. Pat. No. 5,672,662, issued Sep. 30, 1997 (Harris, et al.).

Human NK4 contains 30 free ε-amino groups of 30 lysine residues. When the PEGylation reagent was combined with a SBA compound of Formula II, it has been found that at a protein concentration of about 5 to 10 mg/ml, at a pH of about 7.0 to 8.0, a protein:PEG ratio of about 1:3 and a reaction temperature of from 20-25° C., a mixture of mono-, di-, and trace amounts of the tri-PEGylated species were produced. When the protein:PEG ratio was about 1:1 or 1:2 (for example, preferably about 1:2 for 30 kDa PEG-SBA and about 1:5 for 40 kDa PEG2-NHS), primarily the monoPEGylated species is produced. By manipulating the reaction conditions (e.g., ratio of reagents, pH, temperature, protein concentration, time of reaction etc.), the relative amounts of the different monoPEGylated species can be optimized. Typical, but not limiting, conditions are about 8 to 12 mg/ml NK4, 0.3

M potassium phosphate, pH 8, 25° C., reaction time of 1 h. Under such conditions using 30 kDa PEG-SBA (1:2, protein: PEG), the yield is about 38% monoPEGylated NK4.

Monopegylated NK4 can also be produced according to the methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

Further preferred conjugates according to the invention consist of NK4 protein being covalently linked to a lower-alkoxy poly(ethylene glycol) group via a linker of the formula

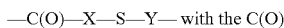

of the linker forming an amide bond with an amino group of NK4 (as mentioned above, the ε-amino group of lysine residues is available), X is —(CH$_2$)$_k$— or —CH$_2$(O—CH$_2$—CH$_2$)$_k$—, k is from 1 to 10, Y is

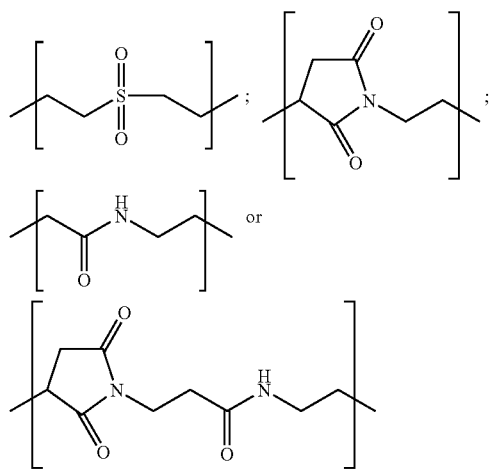

the average molecular weight of the poly(ethylene glycol) moiety is from about 20 kDa to about 40 kDa and the molecular weight of the conjugate is from about 72 kDa to about 92 kDa at a molecular weight of 52 kDa for NK4 polypeptide, or from about 77 kDa to about 97 kDa at a molecular weight of 57 kDa for NK4 glycoprotein.

This NK4 species may also be represented by formula (III)

 (III)

wherein R may be any lower alkyl, by which is meant a linear or branched alkyl group having from one to six carbon atoms such as methyl, ethyl, isopropyl, etc. A preferred alkyl is methyl. X may be —(CH$_2$)$_k$— or —CH$_2$(O—CH$_2$—CH$_2$)$_k$—, wherein k is from 1 to about 10. Preferably, k is from 1 to about 4, more preferably, k is 1 or 2. Most preferably, X is —(CH$_2$).

In formula III, Y is

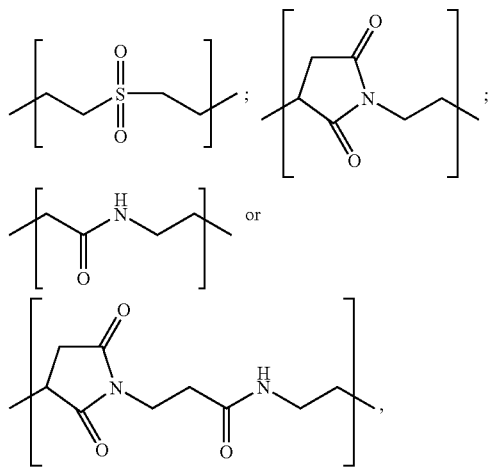

preferably

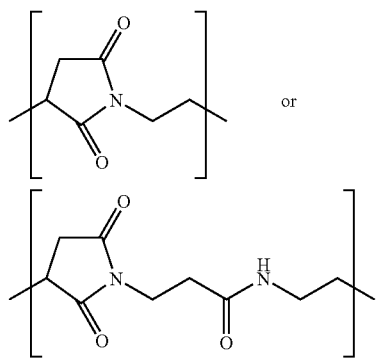

more preferably

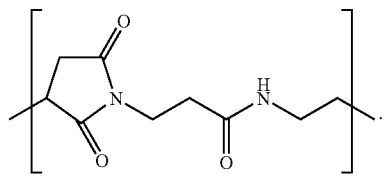

In formula (III), the number m is selected such that the resulting conjugate of formula (III) has a physiological activity comparable to unmodified NK4, which activity may represent the same as, more than, or a fraction of the corresponding activity of unmodified NK4. m represents the number of ethylene oxide chains in the PEG unit. A single PEG subunit of —(OCH$_2$CH$_2$)— has a molecular weight of about 44 daltons. Thus, the molecular weight of the conjugate (excluding the molecular weight of the NK4) depends on the number m. A molecular weight of "about" a certain number means that it is within a reasonable range of that number as determined by conventional analytical techniques. m is therefore an integer ranging from about 450 to about 950 (corresponding to a molecular weight of from about 20 to about 40 kDA).

Preferred NK4 proteins of formula (III) are represented by the formulae:

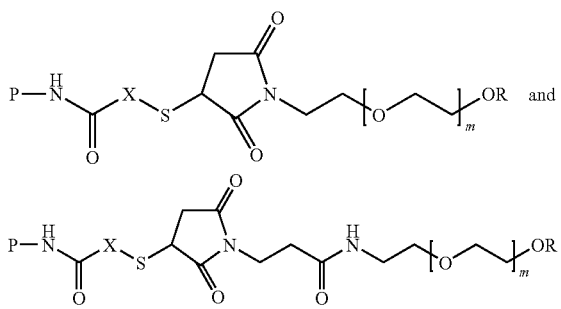

Most preferred NK4 protein products are represented by the formula:

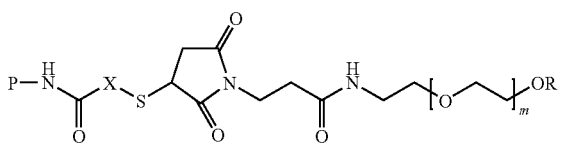

These NK4 proteins may be prepared by (a) covalently reacting a free amino group, preferably an ε-amino group of a lysine amino acid of an NK4 protein or the N-terminal amino group represented by the formula, P—NH$_2$, with a bi-functional reagent represented by the formula, Z—CO—X—S-Q, to form an intermediate with an amide linkage represented by the formula:

P—NH—CO—X—S-Q wherein P is an NK4 protein less the amino group which forms an amide linkage; Z is a reactive group, e.g. a carboxylic-NHS ester; X is —(CH$_2$)$_k$— or —CH$_2$(O—CH$_2$—CH$_2$)$_k$—, wherein k is from 1 to about 10; and Q is a protecting group, like alkanoyl, e.g. acetyl.

(b) covalently reacting the intermediate with an amide linkage from step (a) with an activated polyethylene glycol derivative represented by the formula, W—[OCH$_2$CH$_2$]$_m$—OR, to form an NK4 protein product represented by the formula:

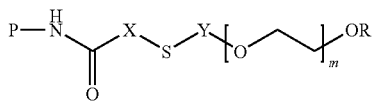

wherein W is a sulfhydryl reactive form of Y; m is an integer ranging from about 450 to about 950; R is lower alkyl; and Y is as defined above.

In this embodiment, the bi-functional reagent is preferably N-succinimidyl-S-acetylthiopropionate or N-succinimidyl-5-acetylthioacetate, Z is preferably N-hydroxy-succinimide, and the activated polyethylene glycol derivative W—[OCH$_2$CH$_2$]$_m$—OR is preferably selected from the group consisting of iodo-acetyl-methoxy-PEG, methoxy-PEG-vinylsulfone, and methoxy-PEG-maleimide.

In more detail, the NK4 proteins of formula (III) may be prepared by covalent linking of a thiol group to NK4 ("activation") and coupling the resulting activated NK4 with a poly(ethylene glycol) (PEG) derivative. The first step for the preparation of monoPEGylated NK4 according to the present invention comprises covalent linking of a thiol group via NH$_2$-groups of NK4. This activation of NK4 is performed with bi-functional reagents which carry a protected thiol group and an additional reactive group, such as active esters (e.g., a succinimidylester), anhydrides, esters of sulphonic acids, halogenides of carboxylic acids and sulphonic acids, respectively. The thiol group is protected by groups known in the art, e.g., acetyl groups. These bi-functional reagents are able to react with the amino groups by forming an amide linkage.

In a preferred embodiment the activation of the amino groups is performed by reaction with bi-functional reagents having a succinimidyl moiety. The bi-functional reagents may carry different spacer species, e.g. —(CH$_2$)$_k$— or —CH$_2$—(O—CH$_2$—CH$_2$—)$_k$— moieties, wherein k is from 1 to about 10, preferably from 1 to about 4, and more preferably 1 or 2, and most preferably 1. Examples of these reagents are N-succinimidyl-S-acetylthiopropionate (SATP) and N-succinimidyl-5-acetylthioacetate (SATA)

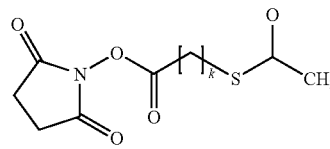

Acetylthioalkyl-carboxylic-NHS-ester, like

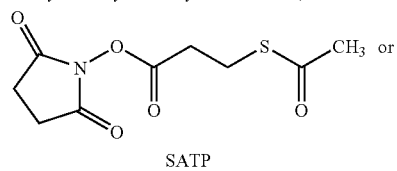

SATP

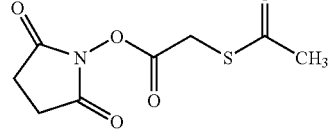

SATA

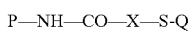

2-(Acetylthio)-(ethoxy)$_k$-acetic-acid-NHS-ester with k as defined above.

The preparation of the bi-functional reagents is known in the art. Precursors of 2-(acetylthio)-(ethoxy)$_k$-acetic-acid-NHS-esters are described in DE-3924705, while the derivatization to the acetylthio compound is described by March, J., Advanced Organic Chemistry (1977) 375-376. SATA is commercially available (Molecular Probes, Eugene, Oreg., USA and Pierce, Rockford, Ill.).

The addition of only one thiol group to an NK4 molecule can be selected by adjusting the reaction parameters, i.e., the protein (NK4) concentration and the protein/bi-functional reagent ratio.

The reaction is carried out, for example, in an aqueous buffer solution, pH 6.5-8.0, e.g., in 10 or 100 mM potassium phosphate, with or without 300 mM NaCl, pH 7.3. The bi-functional reagent may be added in DMSO. After completion of the reaction, preferably after 30 minutes, the reaction is stopped by addition of lysine. Excess bifunctional reagent may be separated by methods known in the art, e.g., by dialysis or column filtration. The average number of thiol groups added to NK4 can be determined by photometric methods described in, for example, Grasetti, D. R., and Murray, J. F. in J. Appl. Biochem. Biotechnol. 119 (1967) 41-49.

The above reaction is followed by covalent coupling of an activated polyethylene glycol (PEG) derivative. Suitable PEG derivatives are activated PEG molecules with an average molecular weight of from about 20 to about 40 kDa.

Activated PEG derivatives are known in the art and are described in, for example, Morpurgo, M., et al. J. Bioconj. Chem. 7 (1996) 363 ff for PEG-vinylsulfone. Linear chain and branched chain PEG species are suitable for the preparation of the compounds of Formula 1. Examples of reactive PEG reagents are iodo-acetyl-methoxy-PEG and methoxy-PEG-vinylsulfone:

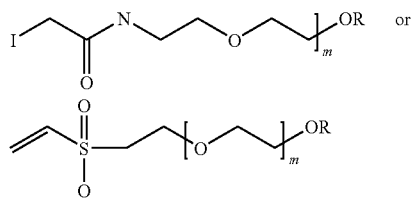

The use of these iodo-activated substances is known in the art and described e.g. by Hermanson, G. T., in Bioconjugate Techniques, Academic Press, San Diego (1996) p. 147-148.

Most preferably, the PEG species are activated by maleimide using (alkoxy-PEG-maleimide), such as methoxy-PEG-maleimide (MW 20,000 to 40,000; Shearwater Polymers, Inc.). The structure of alkoxy-PEG-maleimide is as follows:

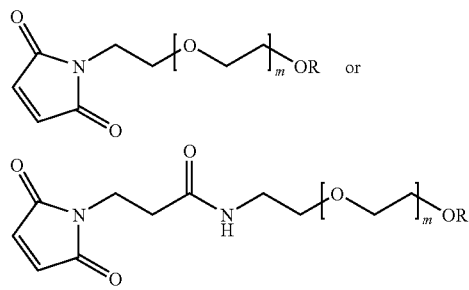

with R and m are as defined above, preferably

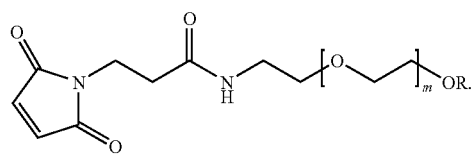

The coupling reaction with alkoxy-PEG-maleimide takes place after in situ cleavage of the thiol protecting group in an aqueous buffer solution, e.g. 10 mM potassium phosphate, 300 mM NaCl, 2 mM EDTA, pH 6.2. The cleavage of the protecting group may be performed, for example, with hydroxylamine in DMSO at 25° C., pH 6.2 for about 90 minutes. For the PEG modification the molar ratio of activated NK4/alkoxy-PEG-maleimide should be from about 1:1 to about 1:6. The reaction may be stopped by addition of cysteine and reaction of the remaining thiol (—SH) groups with N-methylmaleimide or other appropriate compounds capable of forming disulfide bonds. Because of the reaction of any remaining active thiol groups with a protecting group such as N-methylmaleimide or other suitable protecting group, the NK4 proteins in the conjugates of this invention may contain such protecting groups. Generally the procedure described herein will produce a mixture of molecules having varying numbers of thiols protected by different numbers of the protecting group, depending on the number of activated thiol groups on the protein that were not conjugated to PEG-maleimide.

Whereas N-methylmaleimide forms the same type of covalent bond when used to block the remaining thiol-groups on the PEGylated protein, disulfide compounds will lead in an intermolecular sulfide/disulfide exchange reaction to a disulfide bridged coupling of the blocking reagent. Preferred blocking reagents for that type of blocking reaction are oxidized glutathione (GSSG), cysteine and cystamine. Whereas with cysteine no additional net charge is introduced into the PEGylated protein, the use of the blocking reagents GSSG or cystamine results in an additional negative or positive charge.

The further purification of the compounds of formula (III), including the separation of mono- from di-, tri- and multi-PEGylated NK4 species, may be done by methods known in the art, e.g., column chromatography. The percentage of mono-PEG conjugates can be controlled by pooling broader fractions around the elution peak to increase the percentage of mono-PEG in the composition. About ninety percent mono-PEG conjugates is a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

The compounds of the present invention can be formulated according to methods for the preparation of pharmaceutical compositions which methods are known to the person skilled in the art. For the production of such compositions, monoPEGylated NK4 according to the invention is combined in a mixture with a pharmaceutically acceptable carrier. Such acceptable carriers are described, for example, in Remington's Pharmaceutical Sciences, 18th edition, 1990, Mack Publishing Company, edited by Oslo et al. (e.g. pp. 1435-1712). Typical compositions contain an effective amount of the substance according to the invention, for example from about 0.1 to 100 mg/ml, together with a suitable amount of a carrier. The compositions may be administered parenterally.

This invention further provides pharmaceutical compositions comprising monoPEGylated NK4, in which the percentage of mono-PEG conjugates is preferably at least ninety percent, more preferably at least ninety-two percent.

The pharmaceutical compositions according to the invention can be prepared according to known methods in the art. Usually, solutions of monoPEGylated NK4 are dialyzed against the buffer intended to be used in the pharmaceutical composition and the desired final protein concentration is adjusted by concentration or dilution.

Such pharmaceutical compositions may be used for administration for injection and contain an effective amount of the monoPEGylated NK4 together with pharmaceutically acceptable diluents, preservatives, solubilizers, emulsifiers, adjuvants and/or carriers. Such compositions include diluents of various buffer contents (e.g. arginine, acetate, phosphate), pH and ionic strength, additives such as detergents and solubilizing agents (e.g. Tween 80/polysorbate, pluronic F68, sodium chloride, sodium sulfate), antioxidants (e.g. ascorbic acid, L-methionine), preservatives (Timersol, benzyl alcohol) and bulking substances (e.g. saccharose, mannitol), incorporation of the material into particulate preparations of polymeric compounds such as polylactic acid, polyglycolic acid, etc. or into liposomes. Such compositions may influence the physical state stability rate of release and clearance of the monoPEGylated NK4 according to the invention.

The present invention provides for improved NK4 activity and a pharmaceutical composition which can be administered in only a few bolus applications per week and/or in very low dosages, and which are capable of suppressing tumor growth, angiogenesis and metastasis.

It was surprisingly found that the entire amount of randomly PEGylated NK4 according to the invention to be administered during treatment is considerably lower compared to administering unPEGylated NK4. Therefore, the amount of PEGylated NK4 used in pharmaceutical treatment is about 50% or lower, preferably about 20% or lower, and most preferably about 10% or lower than the required amount of unPEGylated NK4.

The invention provides methods for the treatment of human cancer (e.g. breast, lung, prostate, pancreas or colon cancer) characterized in that a pharmaceutically effective amount of monoPEGylated NK4 is administered in one to seven bolus applications per week to the patient in need thereof.

Typically, in a standard cancer treatment regimen, patients are treated with dosages in the range between from 1 to 30 mg of monoPEGylated NK4 per kg per day over a certain period of time, lasting from one day to about 30 days or even longer. Drug is applied as a single daily subcutaneous or i.v. bolus injection of a pharmaceutical formulation containing 0.1 to 100 mg monoPEGylated NK4 per ml. This treatment can be combined with any standard (e.g. chemotherapeutic) treatment, by applying monoPEGylated NK4 before, during or after the standard treatment. This results in an improved outcome compared to standard treatment alone.

In any case the overall amount of administered PEGylated NK4 according to the invention is considerably lower than the amount of NK4 for the same treatment.

The following examples, references and the sequence listing are provided to aid the understanding of the present invention, the true scope of which is set forth in the appended claims. It is understood that modifications can be made in the procedures set forth without departing from the spirit of the invention.

EXAMPLE 1

Recombinant Production of NK4

NK4 for therapeutic uses may be produced by recombinant means using bacterial or eukaryotic expression systems. Suitable eukaryotic expression systems are for example engineered HeLa, BHK or preferably CHO cells. Cells engineered for NK4 production are cultivated in a suitable medium. Typically, a 1 to 5 liter cell culture is used as inoculum for a 10 liter fermenter. After 3 to 5 days, the culture in the 10 liter fermenter can be used as inoculum for the 100 liter fermenter. After additional 3 to 5 days of fermentation, this culture can be used as inoculum for the 1000 liter production fermenter. After 3 to 4 days cells are removed by filtration or centrifugation and discarded. The NK4 containing supernatant is filtered, collected and processed during purification. The purification process is described in the following example.

EXAMPLE 2

Purification

Heparin-Sepharose consists of Separose beads to the surface of which heparin is covalently bound. Since NK4 shows a high affinity to heparin it is retained on this column and can be eluted with high salt concentrations, whereas protein contaminants and other impurities either do not bind or elute at lower salt concentrations. NK4 containing fractions, eluting at about 0.7 to 1.1 M NaCl in 50 mM Hepes pH 7.5 are collected and loaded onto a hydroxyapatite column. NK4 elutes with about 0.4 to 0.7 M potassium phosphate, pH 7.5. The resulting fractions are substantially free of contaminating proteins and can be further purified by S-sepharose chromatography.

EXAMPLE 3

Production of monoPEGylated NK4

NK4 purified in accordance with the above mentioned procedure was used for PEGylation reactions. Three suitable methods are described.

a) PEGylation of NK4 with mPEG-SBA

Aliquots of NK4 were reacted with methoxy-PEG-SBA (5 kDa for comparison, 20 kDa and 30 kDa, respectively; Shearwater Polymers, Inc., Huntsville Ala.). Reaction was carried out at a protein to reagent ratio between 1:1 and 1:5 for about 2 h at room temperature (a ratio of 1:2 is preferred when using 20 and 30 kDa PEG). The reaction was stopped by the addition of 10 mM Tris-buffer or arginine HCl, pH 8, and samples were analyzed by SDS-PAGE or size exclusion chromatography on a Superose 6 column (Pharmacia) using as buffer solution 500 mmol/l potassium phosphate, pH 6.8, for equilibration and elution. The reaction was optimized by varying protein to reagent ratio, pH, time and temperature, in order to obtain predominantly monoPEGylated NK4.

Such conditions are, for example:
Concentration NK4: 8-12 mg/ml
Buffer system/pH: 0.3 M potassium phosphate, pH 8
Temperature: 25° C.
Reaction time: 1 h
Molar ratios (protein:reagent): 1:2
Yield:
MonoPEGylated NK4: 38%
DiPEGylated NK4: 17%
UnPEGylated NK4: 45% b) PEGylation of NK4 with mPEG-SPA

Aliquots of NK4 (protein concentration 8 to 12 mg/ml in 0.3 M potassium phosphate, pH 8) were reacted with methoxy-PEG-SPA (5 kDa for comparison and 20 kDa, respectively; Shearwater Polymers, Inc., Huntsville Ala.). Reaction was carried out at a protein to reagent ratio of 1:2 for about 2 h at room temperature. The reaction was stopped by the addition of 10 mM Tris-buffer or arginine HCl and samples were analyzed by SDS-PAGE, reversed phase HPLC or size exclusion chromatography on a Superose 6 column (Pharmacia) using as buffer solution 500 mmol/l potassium phosphate, pH 6.8, for equilibration and elution. The reaction was optimized by varying protein to reagent ratio, pH, time and temperature, in order to obtain predominantly monoPEGylated NK4, compared to di- and tri-PEGylated NK4.

c) PEGylation of NK4 with mPEG2-NHS

This PEGylation was performed as described in Example 3b with the exception that instead of PEG-SPA, mPEG2-NHS (40 kDa PEG, branched via a lysine linker) was used at a molar ratio of 1:5 (protein:PEG reagent).

EXAMPLE 4

MonoPEGylated

MonoPEGylated NK4 can be separated from unPEGylated, di- and tri-PEGylated NK4 by running a preparative size exclusion chromatography (e.g. Superose 6 or Superdex 200; Pharmacia) using as buffer solution 500 mmol/l K-phosphate pH 6.8, for equilibration and elution, or by ion exchange chromatography. The purified protein contains predominantly the monoPEGylated species. Fractions were collected and analyzed by SDS-PAGE and reversed phase chromatography.

EXAMPLE 5

Molecular Characterization of monoPEGylated NK4 a) Size Exclusion Chromatography

The monoPEGylated species elutes earlier in size exclusion chromatography (e.g. Superose 6 or Superdex 200; Pharmacia; using as buffer solution 500 mmol/l K-phosphate pH 6.8, for equilibration and elution) as compared to the unmodified form. This is due to an increased hydrodynamic radius of the molecule.

b) SDS-PAGE

In SDS-PAGE proteins are separated according to their molecular weight. Due to an increase in molecular weight by PEGylation, the monoPEGylated NK4 shows a shorter migration distance as compared to the unmodified NK4. The migration distance is inversely correlated with the chain length of the PEG moiety and the number of PEG groups attached per NK4 molecule.

c) Peptide Mapping

Digestion of monoPEGylated NK4 with sequence-specific endo-proteinases (e.g. LysC or trypsin) results in a characteristic peptide map. The resulting peptides can be separated by reversed phase chromatography and analyzed by mass spectrometry and/or N-terminal sequencing. This allows for a determination of the PEG-modified groups within the NK4 molecule.

d) Reversed Phase Chromatography

MonoPEGylated NK4 can also be characterized by reversed phase chromatography. PEGylation of NK4 results in a change in retention time as compared to unmodified NK4.

EXAMPLE 6

Comparison of monoPEGylated, unPEGylated and multi-PEGylated NK4

In this example, unPEGylated NK4, NK4 monoPEGylated with PEG 5 kDa, PEG 20 kDa, PEG 30 kDa, PEG 40 kDa and multiPEGylated NK4 (NK4 PEGylated with more than one PEG chain) were used.

a) Scatter Assay

MDCK cells were subconfluently grown in tissue culture plates. Cells were treated with HGF (10 ng/ml) or with combinations of HGF and NK4. In these experiments the HGF-induced cell scattering was inhibited by the addition of a 10 to 1000-fold molar excess of NK4, showing the functional activity of PEGylated NK4. It was found that the in vitro activity of monoPEGylated 5 kDa-PEG-NK4, 20 kDa-PEG-NK4, 30 kDa-PEG-NK4, and 40 kDa-PEG-NK4 is similar to unPEGylated NK4. It was also found that the addition of more than one PEG chain (20 to 40 kDa) results in a significant loss of in vitro activity (Table 1).

TABLE 1

Scores of the MDCK scatter assay

| NK4 (µg/ml) | NK4 (control) | | 40 kDa-PEG-NK4 | | | 30 kDa-PEG-NK4 | | | |
|---|---|---|---|---|---|---|---|---|---|
| | NK4 | NK4 | Mono-PEG | Di-PEG | Tri-PEG | Mono-PEG | Di- and Tri-PEG | Tri- and Tetra-PEG | Penta-PEG |
| 5.00 | ++ | ++ | ++ | + | +/− | ++ | ++ | + | − |
| 1.67 | ++ | ++ | ++ | + | − | ++ | + | +/− | − |
| 0.56 | ++ | ++ | ++ | +/− | − | ++ | + | − | − |
| 0.19 | + | + | + | − | − | + | +/− | − | − |
| 0.06 | +/− | +/− | +/− | − | − | +/− | − | − | − |
| 0.02 | − | − | − | − | − | − | − | − | − |

| NK4 (µg/ml) | 20 kDa-PEG-NK4 | | | 5 kDa-PEG-NK4 | | | | | | |
|---|---|---|---|---|---|---|---|---|---|---|
| | Mono-PEG | Di-PEG | Tri-PEG | Mono-PEG | Di-PEG | Tri-PEG | Tetra-PEG | Penta-PEG | Hexa-PEG | Hepta-PEG |
| 5.00 | ++ | ++ | + | ++ | ++ | ++ | ++ | + | − | − |
| 1.67 | ++ | + | + | ++ | ++ | ++ | ++ | + | − | − |
| 0.56 | ++ | + | +/− | ++ | ++ | + | + | +/− | − | − |
| 0.19 | + | +/− | − | + | + | + | +/− | − | − | − |
| 0.06 | +/− | − | − | +/− | +/− | − | − | − | − | − |
| 0.02 | − | − | − | − | − | − | − | − | − | − |

The relative potency of various PEGylated forms of NK4 in the inhibition of HGF (10 ng/ml)-induced scattering of MDCK cells was assayed. ++ means complete inhibition, + means inhibition, +/− means weak inhibition and − means no inhibition.

b) HUVEC Proliferation Assay

Figure 2:
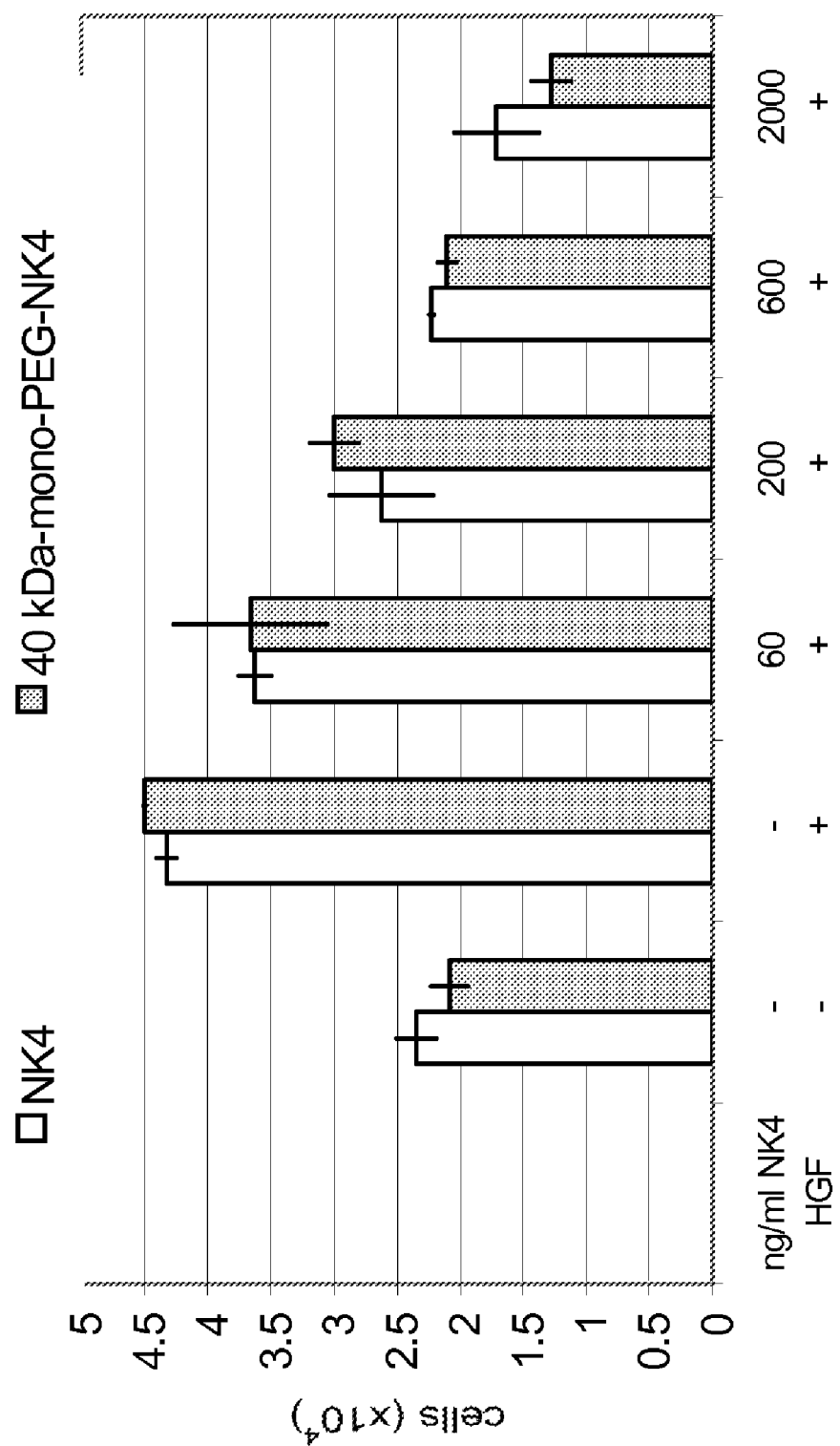
FIG. 2 Inhibition of HGF-induced HUVEC proliferation by NK4 and 40 kDa-mono-PEG-NK4.

Inhibition of the mitogenic activity of HGF by NK4 was determined by measuring proliferation of HUVECs in culture as described in Nakamura, T., et al., Nature 342 (1989) 440-443. In these experiments the HGF-induced cell proliferation was inhibited by the addition of a 10 to 1000-fold molar excess of NK4, showing the functional activity of monoPEGylated NK4 (FIGS. 1 and 2).

Figure 3:
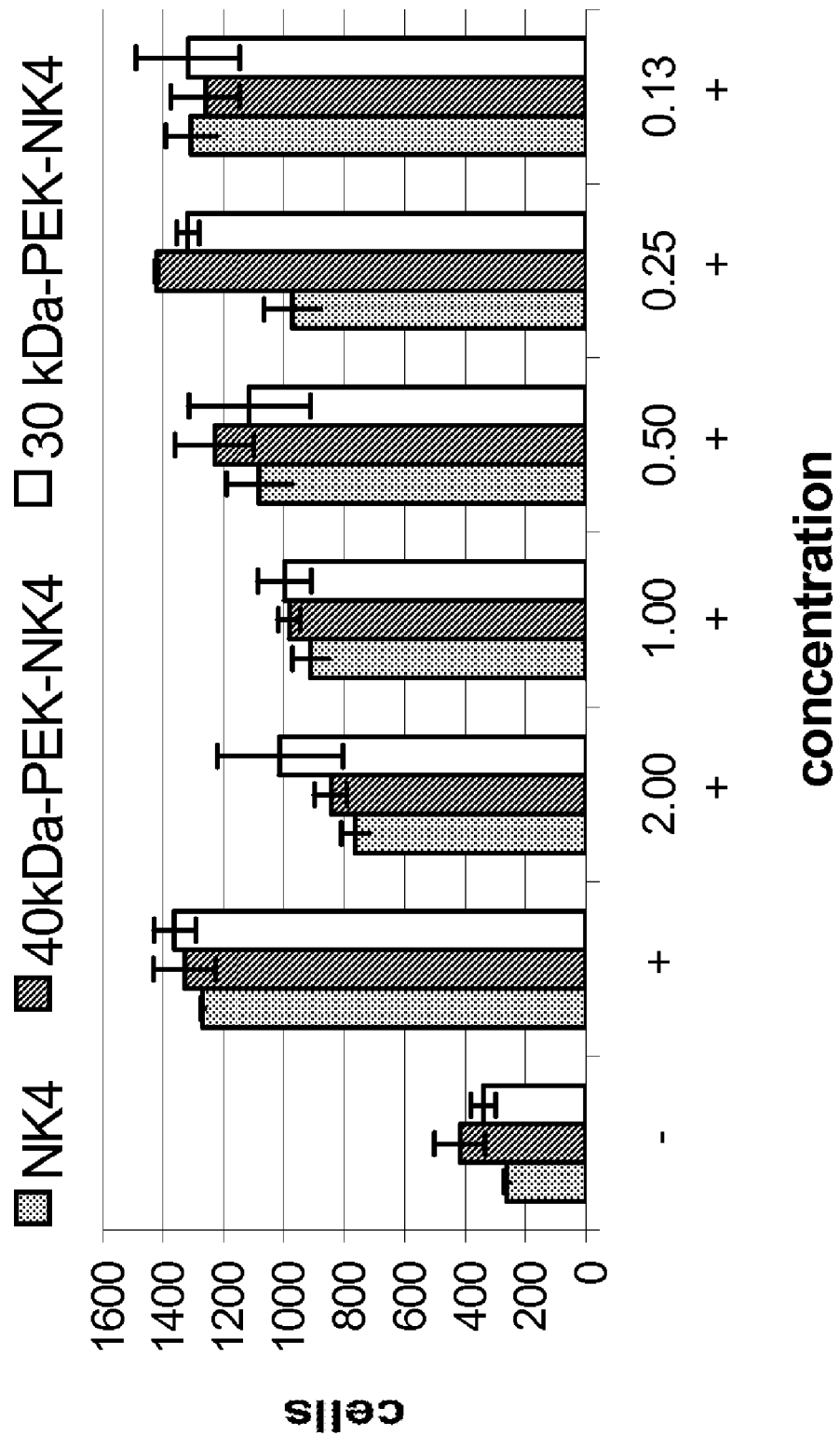
FIG. 3 Inhibition of bFGF-induced HUVEC proliferation by NK4, 30 kDa-mono-PEG-NK4 and 40 kDa-mono-PEG-NK4.

Alternatively, the HUVEC Proliferation assay was performed by inhibition of the mitogenic activity of bFGF (basic fibroblastic growth factor) by NK4. Inhibition was determined by measuring proliferation of HUVECs in culture as described in Kuba, K., et al., Cancer Res. 60 (2000) 6737-6743. In these experiments the FGF-induced cell proliferation was inhibited by the addition of a 10 to 1000-fold molar excess of NK4, showing the functional activity of monoPEGylated NK4 (FIG. 3).

c) Invasion Assay

In this assay the invasive potential of tumor cells is analyzed. The assay was done essentially as described in Albini, A., et al. (1987) using HT 115 cells. Again, HGF-induced (10 ng/ml) cell invasion could be inhibited by a 10 to 1000-fold molar excess of PEGylated NK4, showing the functional activity of monoPEGylated NK4.

EXAMPLE 7

Activity In Vivo

Model: Panc Tu1 human pancreatic cancer orthotopic SCID mouse model (Alves, F., et al., Pancreas 23 (2001) 227-235).

Treatment: After 8 days, one application daily of monoPEGylated NK4 over a period of 21 days.

Doses: 16 mg/kg/day
4 mg/kg/day
1 mg/kg/day
Placebo

Result: Treatment with monoPEGylated NK4 shows a dose-dependent suppression of primary tumor growth compared to placebo treated groups. For example, with a dose of 4 mg/kg/day of monoPEGylated NK4, a tumor volume of only 200 mm$^3$ was found compared to a tumor volume of 280 mm$^3$ in the placebo treated animal group.

EXAMPLE 8

Pharmaceutical Composition

Suitable pharmaceutical compositions are, for example:

1 to 30 mg/ml monoPEGylated NK4

150 mM NaCl 10 mM sodium phosphate, pH 7.2

1 to 30 mg/ml monoPEGylated NK4

150 mM NaCl 0.01% Tween 80 or Tween 20 or pluronic F68

10 mM sodium phosphate, pH 7.2

1 to 30 mg/ml monoPEGylated NK4

50 mM NaCl

3% mannitol 10 mM sodium phosphate, pH 7.2

1 to 30 mg/ml monoPEGylated NK4

50 mM NaCl

3% mannitol 0.01% Tween 80 or Tween 20 or pluronic F68

10 mM sodium phosphate, pH 7.2

The compositions are prepared in that monoPEGylated NK4 is dialyzed against the above mentioned buffer solution (with or without mannitol). The protein concentration is adjusted by concentration or dilution with the buffer solution. Detergent and NaCl are added out of a 10% stock solution.

EXAMPLE 9

Pharmacokinetic Analysis of NK4, 30 kDa-mono-PEG-NK4 and 40 kDa-mono-PEG-NK4

Figure 4A:
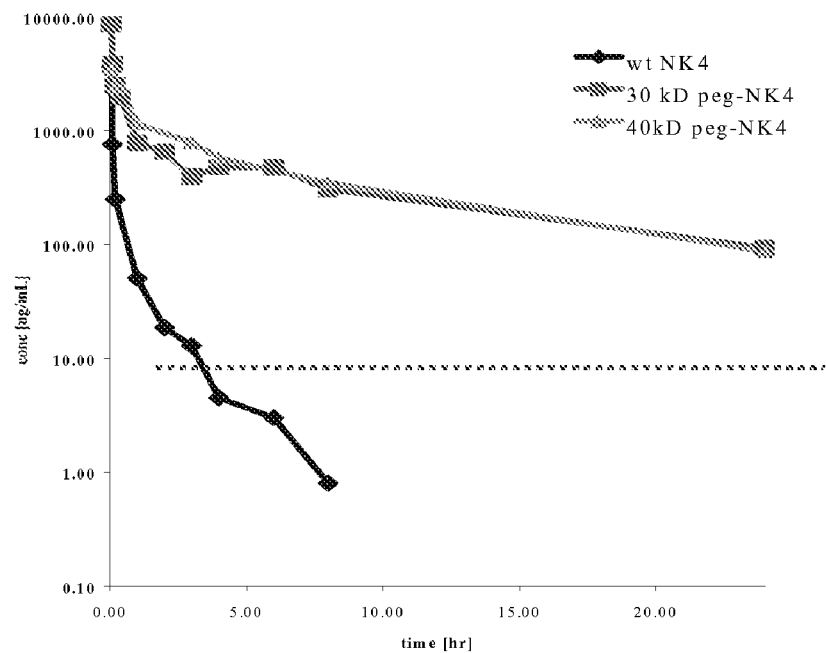
FIG. 4A Time-concentration curve of NK4, 30 kDa-monoPEG-NK4, 40 kDa-mono-PEG-NK4 in plasma after i.v. administration.
Figure 4B:
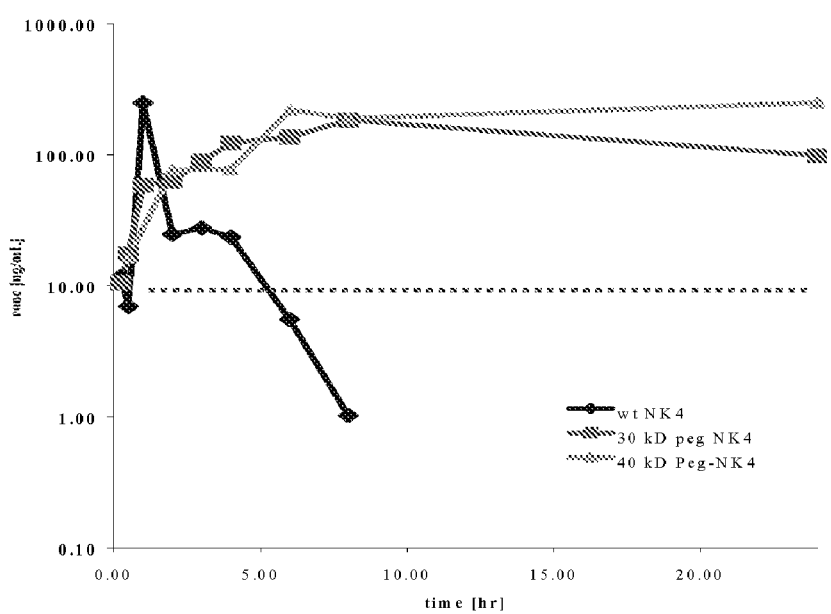
FIG. 4B Time-concentration curve of NK4, 30 kDa-monoPEG-NK4, 40 kDa-mono-PEG-NK4 in plasma after s.c. injection.

Adult mice (4 per group) received single i.v. or s.c. bolus injections of NK4, 30 kDa-mono-PEG-NK4 or 40 kDa-mono-PEG-NK4 (4 mg/kg in 0.25 ml injection volume), respectively. At several time points blood samples were taken and analyzed for NK4, 30 kDa-mono-PEG-NK4 or 40 kDa-mono-PEG-NK4 content by ELISA. The time-concentration curves were calculated and are shown in FIGS. 4A and 4B. These data show that 30 kDa-mono-PEG-NK4 and 40 kDa-mono-PEG-NK4 have significantly improved stability in vivo, resulting in significantly increased plasma half-lives compared to unmodified NK4.

What is claimed is:

1. A composition comprising conjugates consisting of a N-terminal 447 amino acids of the Hepatocyte Growth Factor (HGF/SF)α-chain (NK4) molecule and a single polyethylene glycol group having a molecular weight of from about 30 to about 40 kDa, wherein said polyethylene glycol group has the formula

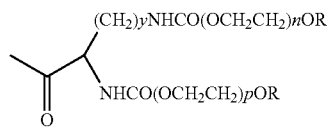

$(CH_2)_y NHCO(OCH_2CH_2)_n OR$ $NHCO(OCH_2CH_2)_p OR$ and said —CO group randomly forms an amide bond with one of the amino groups of the N-terminal fragment of said NK4 molecule, wherein
y is from 1 to 10;
n and p together are from about 450 to about 950; and
R is $(C_1-C_6)$alkyl,
wherein said monoPEGylated conjugates comprise at least 92% of the total of pegylated NK4 molecules and unpegylated NK4 molecules in the composition, and further comprising 1 to 30 mg/ml monoPEGylated NK4, 150 mM NaCl, 10 mM sodium phosphate and a pH of 7.2.

2. The composition of claim 1, further comprising 0.01% Tween 80, Tween 20 or pluronic F68.

3. A composition comprising conjugates consisting of a N-terminal 447 amino acids of the Hepatocyte Growth Factor (HGF/SF)α-chain (NK4) molecule and a single polyethylene glycol group having a molecular weight of from about 30 to about 40 kDa, wherein said polyethylene glycol group has the formula

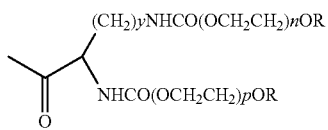

and said —CO group randomly forms an amide bond with one of the amino groups of the N-terminal fragment of said NK4 molecule,
wherein
y is from 1 to 10;
n and p together are from about 450 to about 950; and
R is $(C_1-C_6)$alkyl, wherein said monoPEGylated conjugates comprise at least 92% of the total of pegylated NK4 molecules and unpegylated NK4 molecules in the composition, and further comprising 1 to 30 mg/ml monoPEGylated NK4, 50 mM NaCl, 3% mannitol, 10 mM sodium phosphate and a pH of 7.2.

4. The composition of claim 3, further comprising 0.01% Tween 80, Tween 20 or pluronic F68.

5. A method for the treatment of cancer wherein 1 to 30 mg of the monoPEGylated NK4 conjugate of claim 1 is administered per kg per day to a patient in need thereof.

6. The method of claim 5, wherein the cancer is selected form the group consisting of breast, lung, prostate, pancreas or colon cancer.

7. The method of claim 6, wherein the cancer is pancreas cancer.

* * * * *

SEQUENCE LISTING

```
<160> NUMBER OF SEQ ID NOS: 2

<210> SEQ ID NO 1
<211> LENGTH: 1344
<212> TYPE: DNA
<213> ORGANISM: homo sapiens

<400> SEQUENCE: 1
caaaggaaaa gaagaaatac aattcatgaa ttcaaaaaat cagcaaagac taccctaatc      60
aaaatagatc cagcactgaa gataaaaacc aaaaaagtga atactgcaga ccaatgtgct     120
```

-continued

```
aatagatgta ctaggaataa aggacttcca ttcacttgca aggcttttgt ttttgataaa    180
gcaagaaaac aatgcctctg gttccccttc aatagcatgt caagtggagt gaaaaaagaa    240
tttggccatg aatttgacct ctatgaaaac aaagactaca ttagaaactg catcattggt    300
aaaggacgca gctacaaggg aacagtatct atcactaaga gtggcatcaa atgtcagccc    360
tggagttcca tgataccaca cgaacacagc ttttttgcctt cgagctatcg ggtaaagac    420
ctacaggaaa actactgtcg aaatcctcga ggggaagaag ggggaccctg tgtttcaca    480
agcaatccag aggtacgcta cgaagtctgt gacattcctc agtgttcaga agttgaatgc    540
atgacctgca atggggagag ttatcgaggt ctcatggatc atacagaatc aggcaagatt    600
tgtcagcgct gggatcatca gacaccacac cggcacaaat tcttgcctga agatatccc    660
gacaagggct ttgatgataa ttattgccgc aatcccgatg ccagccgag ccatggtgc     720
tatactcttg accctcacac ccgctgggag tactgtgcaa ttaaaacatg cgctgacaat    780
actatgaatg acactgatgt ccctttggaa acaactgaat gcatccaagg tcaaggagaa    840
ggctacaggg gcactgtcaa taccatttgg aatggaattc catgtcagcg ttgggattct    900
cagtatcctc acgagcatga catgactcct gaaaatttca gtgcaagga cctacgagaa    960
aattactgcc gaaatccaga tgggtctgaa tcaccctggt gttttaccac tgatccaaac   1020
atccgagttg ctactgctc ccaaattcca aactgtgata tgtcacatgg acaagattgt   1080
tatcgtggga atggcaaaaa ttatatgggc aacttatccc aaacaagatc tggactaaca   1140
tgttcaatgt gggacaagaa catggaagac ttacatcgtc atatcttctg gaaccagat   1200
gcaagtaagc tgaatgagaa ttactgccga atccagatg atgatgctca tggaccctgg   1260
tgctacacgg gaaatccact cattccttgg gattattgcc ctatttctcg ttgtgaaggt   1320
gataccacac ctacaatagt ctaa                                          1344
```

<210> SEQ ID NO 2
<211> LENGTH: 447
<212> TYPE: PRT
<213> ORGANISM: homosapiens

<400> SEQUENCE: 2

```
Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
```

-continued

```
145                 150                 155                 160
Ser Asn Pro Glu Val Arg Tyr Glu Val Cys Asp Ile Pro Gln Cys Ser
                165                 170                 175
Glu Val Glu Cys Met Thr Cys Asn Gly Glu Ser Tyr Arg Gly Leu Met
                180                 185                 190
Asp His Thr Glu Ser Gly Lys Ile Cys Gln Arg Trp Asp His Gln Thr
                195                 200                 205
Pro His Arg His Lys Phe Leu Pro Glu Arg Tyr Pro Asp Lys Gly Phe
                210                 215                 220
Asp Asp Asn Tyr Cys Arg Asn Pro Asp Gly Gln Pro Arg Pro Trp Cys
225                 230                 235                 240
Tyr Thr Leu Asp Pro His Thr Arg Trp Glu Tyr Cys Ala Ile Lys Thr
                245                 250                 255
Cys Ala Asp Asn Thr Met Asn Asp Thr Asp Val Pro Leu Glu Thr Thr
                260                 265                 270
Glu Cys Ile Gln Gly Gln Gly Glu Gly Tyr Arg Gly Thr Val Asn Thr
                275                 280                 285
Ile Trp Asn Gly Ile Pro Cys Gln Arg Trp Asp Ser Gln Tyr Pro His
                290                 295                 300
Glu His Asp Met Thr Pro Glu Asn Phe Lys Cys Lys Asp Leu Arg Glu
305                 310                 315                 320
Asn Tyr Cys Arg Asn Pro Asp Gly Ser Glu Ser Pro Trp Cys Phe Thr
                325                 330                 335
Thr Asp Pro Asn Ile Arg Val Gly Tyr Cys Ser Gln Ile Pro Asn Cys
                340                 345                 350
Asp Met Ser His Gly Gln Asp Cys Tyr Arg Gly Asn Gly Lys Asn Tyr
                355                 360                 365
Met Gly Asn Leu Ser Gln Thr Arg Ser Gly Leu Thr Cys Ser Met Trp
                370                 375                 380
Asp Lys Asn Met Glu Asp Leu His Arg His Ile Phe Trp Glu Pro Asp
385                 390                 395                 400
Ala Ser Lys Leu Asn Glu Asn Tyr Cys Arg Asn Pro Asp Asp Asp Ala
                405                 410                 415
His Gly Pro Trp Cys Tyr Thr Gly Asn Pro Leu Ile Pro Trp Asp Tyr
                420                 425                 430
Cys Pro Ile Ser Arg Cys Glu Gly Asp Thr Thr Pro Thr Ile Val
                435                 440                 445
```